US00RE49658E

(19) United States
(12) Reissued Patent
Mayse et al.

(10) Patent Number: US RE49,658 E
(45) **Date of Reissued Patent: *Sep. 19, 2023**

(54) INTERCOSTAL PUMP

(71) Applicant: CRM Pulmonology Tech, LLC, Wayzata, MN (US)

(72) Inventors: Martin Mayse, Wayzata, MN (US); Ryan Smith, Berkeley, CA (US); Chris Butts, Wilmette, IL (US)

(73) Assignee: CRM PULMONOLOGY TECH, LLC, Wayzata, MN (US)

( * ) Notice: This patent is subject to a terminal disclaimer.

(21) Appl. No.: 17/334,633

(22) Filed: May 28, 2021

Related U.S. Patent Documents

Reissue of:
(64) Patent No.: 10,300,255
Issued: May 28, 2019
Appl. No.: 15/168,269
Filed: May 31, 2016

U.S. Applications:
(63) Continuation of application No. 13/968,479, filed on Aug. 16, 2013, now Pat. No. 9,393,387.

(60) Provisional application No. 61/684,101, filed on Aug. 16, 2012.

(51) Int. Cl.
*A61M 27/00* (2006.01)
*A61M 39/22* (2006.01)

(52) U.S. Cl.
CPC ..... *A61M 27/002* (2013.01); *A61M 27/006* (2013.01); *A61M 39/22* (2013.01); *A61M 2210/101* (2013.01); *A61M 2210/1017* (2013.01)

(58) Field of Classification Search
CPC ..... A61M 27/008; A61M 27/006; A61M 2027/004; A61M 27/00; A61M 27/002
See application file for complete search history.

(56) References Cited

U.S. PATENT DOCUMENTS

| | | | |
|---|---|---|---|
| 3,683,929 | A | 8/1972 | Holter |
| 4,850,955 | A | 7/1989 | Newkirk |
| 5,009,635 | A | 4/1991 | Scarberry |
| 5,830,172 | A | 11/1998 | Leveen |

OTHER PUBLICATIONS

Notice of Allowance and Reasons for Allowance for U.S. Appl. No. 13/968,479, dated Mar. 24, 2016, 8 pages.
"Office Action for U.S. Appl. No. 13/968,479, dated Sep. 23, 2015, 9 pages".

*Primary Examiner* — Beverly M Flanagan
(74) *Attorney, Agent, or Firm* — Lee Sullivan Shea & Smith LLP

(57) ABSTRACT

An intercostal-pump based fluid management system, as described herein, comprises an intercostal pump that is, generally, a resiliently flexible bulb having an inlet and an outlet. The inlet is attached to a first tube that extends from the intercostal pump to a first area of a patient's body, for example, the patient's pleural cavity. The outlet is connected to a second tube that extends from the intercostal pump to a second area of a patient's body, for example, the patient's peritoneal cavity. In use, the intercostal pump is placed between a first rib and a second rib in a patient. The intercostal pump operates by being successively compressed and decompressed between the first and second ribs as the patient breaths.

30 Claims, 12 Drawing Sheets

INTERCOSTAL PUMP

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This *is a reissue* application *of U.S. patent application Ser. No. 15/168,269 filed on May 31, 2016, entitled "Intercostal Pump," and issued as U.S. Pat. No. 10,300,255, which* claims priority to U.S. patent application Ser. No. 13/968,479 filed on Aug. 16, 2013, entitled "Systems and Methods for Draining Bodily Fluid via an Intercostal Pump," *and issued as U.S. Pat. No. 9,393,387,* which is incorporated herein in its entirety. U.S. patent application Ser. No. 13/968,479 claims priority to U.S. Provisional Patent Application Ser. No. 61/684,101 filed Aug. 16, 2012, entitled "Systems and Methods for Draining Bodily Fluid via an Intercostal Pump," which is also incorporated herein in its entirety.

BACKGROUND

A number of well-known techniques for draining bodily fluid involve utilizing a pump, in combination with a shunt or catheter, to drain fluid from one cavity within the human body to either another cavity or to a reservoir outside of the body. Such techniques may be utilized for purposes including, for example, draining a patient's blood, urine, saliva, cerebrospinal fluid, peritoneal fluid, and/or pleural fluid, among other possibilities.

One common drainage-technique application is the drainage of pleural fluid for the treatment of pleural effusions. Pleural fluid is normally a low-protein liquid that can be found in relatively small amounts (normally a few milliliters) in a patient's pleural cavity. The pleural cavity is the space between the visceral pleura (i.e., the membrane surrounding each lung) and the parietal pleura (i.e., the membrane lining the inside of the rib cage). Pleural fluid provides a lubricating function during the breathing process and, normally, a patient's body constantly produces and absorbs pleural fluid. However, under certain abnormal conditions, such as infection, inflammation, malignancy, heart failure, liver failure, or kidney failure, among other conditions, the net flow of pleural fluid within the pleural cavity becomes unbalanced resulting in the excess accumulation (e.g., on the order of liters) of fluid in the pleural space.

Excess accumulation of pleural fluid is known as pleural effusion and may cause the pathological compression of one or both lungs-resulting in considerable difficulty or prevention of the breathing process in either or both lungs. Pleural effusion may lead to, for example, dyspnea, shortness of breath, chest pain, and/or chronic cough, greatly compromising a patient's quality of life.

Currently, pleural effusions affect approximately 1.4 million new patients each year. Over 200,000 of such pleural effusions result from malignancy and are seriously dangerous to the patients' health. More than one half of those patients with malignant pleural effusions have symptoms resulting directly from their effusion.

One treatment option for recurrent, symptomatic pleural effusions is repeated therapeutic thoracentesis. Thoracentesis involves passing a needle and catheter apparatus into the pleural cavity, at which point the needle is removed, leaving the catheter in the pleural space. The catheter remains in place and, thereby, acts as a drainage tube that leads the excess pleural fluid to a collection reservoir outside of the body. This procedure typically improves symptoms significantly. Unfortunately, malignant effusions are likely to recur and, due to patients' delays in notifying their physician that their symptoms have returned and delays in providing repeat thoracentesis, patients often spend a significant portion of their life with effusion-related symptoms. Furthermore, thoracentesis is painful and uncomfortable, and is frequently accompanied by threatening or debilitating complications, such as pneumothorax (i.e., the collapse of the lung due to accumulation of air in the pleural cavity) in up to eleven percent of patients and severe bleeding or infection in many others.

Another treatment option is chest-tube pleurodesis, which involves the obliteration of the pleural space by the instillation of a sclerosant agent via a chest tube. In this approach, a chest tube is inserted into the patient under moderate sedation or general anesthesia and the pleural fluid is drained, in a manner similar to the drainage achieved in thoracentesis. After drainage of the pleural effusion a sclerosing agent is instilled through the tube into the pleural cavity to completely coat the visceral and parietal membranes so that these membranes will permanently adhere to each other to close and eliminate the pleural cavity. Chest-tube pleurodesis can sometimes lead to long-term control of effusion-related symptoms. Unfortunately, chest-tube pleurodesis typically requires hospitalization for at least two days and as many as seven days, can be quite painful, can lead to breathing difficulties of it's own, and, in up to one third of patients, fails to provide relief of symptoms for more than a few weeks.

One variation of chest-tube pleurodesis is thoracoscopic pleurodesis, which involves the insertion of a telescope into the patient's chest by way of an intercostal incision on the patient's side. Pleural fluid is evacuated and a detailed inspection of the pleural space is undertaken so as to more discriminately apply sclerosant to regions of abnormality. In some cases, thoracoscopic pleurodesis can achieve better results than even chest-tube pleurodesis. Unfortunately, thoracoscopic pleurodesis typically requires hospitalization for four to seven days.

Yet another treatment option is chronic indwelling pleural catheters. Such indwelling catheters are placed in the patient permanently, allowing a patient to drain pleural fluid to an external reservoir on an intermittent, yet continual, basis. That is, while the pleural catheter is placed substantially inside the patient, the catheter also extends outside of the patient's body and may remain externally exposed for extended period of times. Chronic indwelling catheters have been shown to result in relatively high success rates in the management of effusion-related symptoms, and are associated with relatively short patient-hospital times of approximately one day. However, a considerable percentage of patients, approximately eight percent, fall victim to infection. Further, the patient is subject to the discomfort, irritation, and annoyance of an exposed indwelling catheter that transmits fluid to an external reservoir.

Related to indwelling pleural catheters, pleuroperitoneal shunts provide a permanent conduit between the pleural cavity and the peritoneal cavity, or the abdomen, which allows fluid to move from the pleural cavity to the peritoneal cavity, as opposed to an external reservoir. Once in the peritoneal cavity, the fluid is reabsorbed into the patients blood steam through blood and lymph vessels located in the abdomen. In popular pleuroperitoneal shunts, the shunt has a pumping chamber that must be manually activated by the patient or caregiver to move the pleural fluid. The pleuroperitoneal shunt is tunneled under the skin from the chest to the abdomen with the pumping chamber lodged in a subcutaneous pocket overlying the costal margin, or lower edge, of the rib cage. Pleuroperitoneal shunts, like chronic indwelling catheters, have been shown to result in relatively high success rates in the management of effusion-related symptoms, and are associated with relatively short patient-hospital times of approximately one day. However, also like chronic indwelling catheters, a considerable percentage of patients, approximately four percent, fall victim to infection. Further drawbacks of conventional pleuroperitoneal shunts include a relatively high rate of shunt-specific complications, such as clotting of fluid within the shunt, as well as the discomfort and inconvenience arising from manual activation of the pump by the patient.

OVERVIEW

Accordingly, there is a need for a novel technique of draining pleural fluid that provides for a high rate of success in treating pleural effusions, and avoids high rates of infection and other complications, doesn't require lengthy patient-hospital times and/or repeated hospital visits, and avoids the inconvenience of both manually activated pumps and external reservoirs. A fluid management system based on an intercostal pump, as described herein, provides for such a novel and beneficial drainage technique.

An intercostal-pump based fluid management system, as described herein, comprises an intercostal pump that is, generally, a resiliently flexible bulb having an inlet and an outlet. The inlet is attached to a first tube that extends from the intercostal pump to a first area of a patient's body, for example, the patient's pleural cavity. The outlet is connected to a second tube that extends from the intercostal pump to a second area of a patient's body. The second area of the patients' body may be, for example, the patient's peritoneal cavity. Upon operation of the intercostal pump, fluid is transferred from the first area of the patient's body to the second area.

In use, the intercostal pump is placed between a first rib and a second rib in a patient. (Note that although the terms "first rib" and "second rib" are used herein, it should be understood that such use does not necessarily refer to any particular two ribs, e.g. the "first" and "second" ribs as typically referred to in anatomical contexts as the two ribs nearest a patients' skull.) The intercostal pump operates by being successively compressed and decompressed between the first and second ribs as the patient breaths. As the patient inhales, the patient's rib cage expands and the intercostal pump is decompressed. As the patient exhales, the patient's rib cage contracts and the intercostal pump is compressed.

Use of an intercostal pump as described herein avoids certain shortcomings of known fluid drainage techniques. For instance, the intercostal pump operates to drain fluid regularly, continuously, and automatically without requiring a patient to manually compress a pump by hand or requiring a patient to drain fluid external to the patient's body. Further, due to the continuous operation of the intercostal pump, improved performance may be achieved by decreasing the occurrence of clotting observed in other fluid-drainage systems that may remain inactive for long periods of time.

BRIEF DESCRIPTION OF DRAWINGS

The invention disclosed herein will be more readily understood from a reading of the specification with reference to the accompanying drawings forming a part thereof, wherein.

DETAILED DESCRIPTION

The apparatuses, systems, and methods described herein may be used for the purposes of draining fluid from one cavity within the human body to another cavity. More particularly, the apparatuses, systems, and methods described herein comprise an intercostal pump which provides a general pumping function in an intercostal-pump based fluid management system.

For purposes of explanation, the disclosure herein includes a discussion of the use of an intercostal-pump based fluid management system for the purposes of drainage of pleural fluid for the treatment of pleural effusions. However, it should be understood that such an application is but one particular application of one particular embodiment of an intercostal-pump based fluid management system, and that other embodiments and applications are certainly possible as well.

Also, for purposes of explanation, the disclosure herein describes an intercostal pump as part of a particular exemplary intercostal-pump based fluid management systems. However, it should be understood that any such intercostal-pump based fluid management system disclosed herein is but a particular embodiment of an intercostal-pump based fluid management system that uses an intercostal pump as described herein, and that other uses of an intercostal pump are certainly possible as well.

The intercostal-pump based fluid management system provides for regular, continuous, and automatic drainage of bodily fluid. Therefore, many of the disadvantages of other techniques for draining bodily fluid may be avoided.

1. INTERCOSTAL-PUMP BASED FLUID MANAGEMENT SYSTEM

Figure 1A:
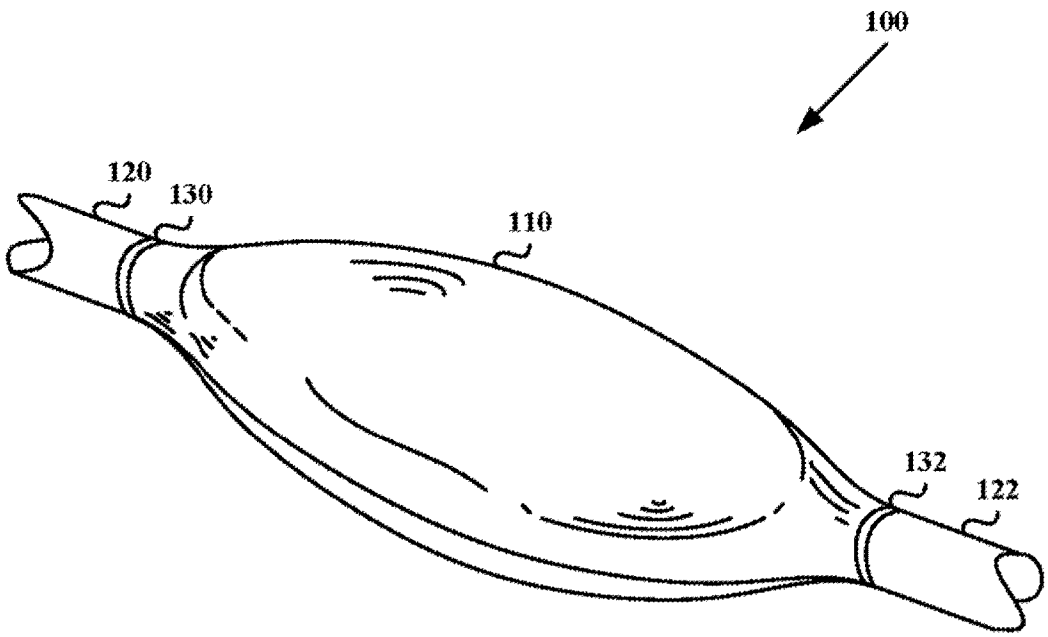
FIGS. 1A, 1B, and 1C show a perspective view of an exemplary intercostal-pump based fluid management system including an exemplary intercostal pump and also including inlet and outlet catheters shortened for illustrative purposes.
Figure 1B:
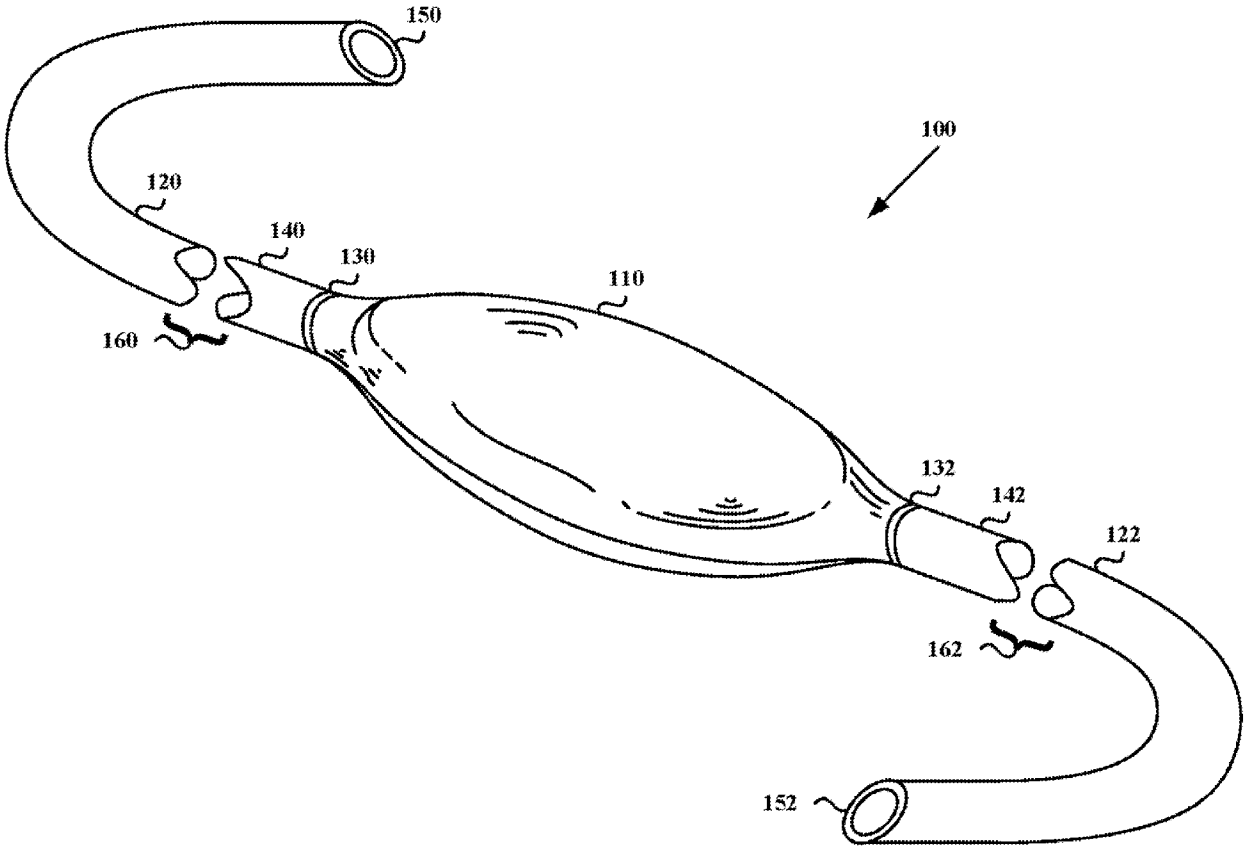
Figure 1C:
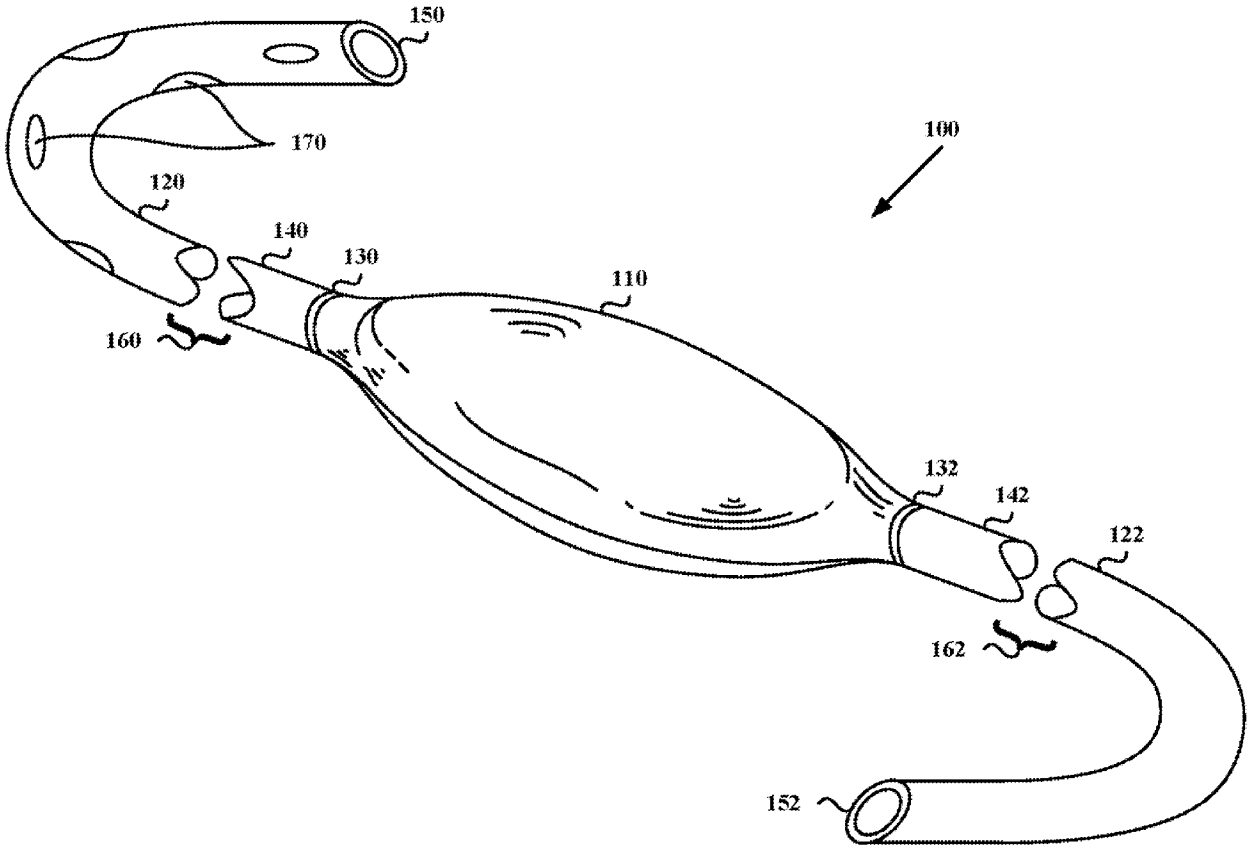

FIGS. 1A, 1B, and 1C show a perspective view of an exemplary intercostal-pump based fluid management system including an exemplary intercostal pump and also including inlet and outlet catheters (the depiction of which have been shortened in length for illustrative purposes). It should be understood that FIGS. 1A, 1B, and 1C show an embodiment of an intercostal-pump based fluid management system for purposes of explanation and that other embodiments are certainly possible as well.

a. Intercostal-Pump Based Fluid Management System Generally

With reference to FIG. 1A, intercostal-pump based fluid management system 100 comprises intercostal pump 110. Intercostal pump 110 is, generally, a resiliently flexible bulb enclosing an interior space and having an inlet 130 and an outlet 132. Intercostal pump 100 may be made of any suitable material that allows for intercostal pump 100 to be compressed and then freely returned to its original state. For example, intercostal pump 110 may be a resiliently flexible bulb made of polyurethane, silicone, polyvinyl chloride, or latex rubber.

Although intercostal pump 110 is shown as a generally spherical, or ovular, bulb, other configurations are certainly possible as well. In short, intercostal pump 110 may be any shape providing for suitable compression/decompression and placement in an intercostal region. In particular, it may 5 be desirable to conform, to some extent, intercostal pump 110, to the characteristics (i.e., shape and/or space) of a particular intercostal region. In an embodiment, intercostal pump 110 may comprise flexible silicone tubing. Intercostal pump 110 may take other forms as well.

Intercostal pump 110 is discussed in greater detail below.

Intercostal-based fluid management system 100 also comprises a first tube 120 and a second tube 122. Inlet 130 and outlet 132 communicate between the interior and the exterior of intercostal pump 110 and are coupled to the first tube 120 and the second tube 122, respectively. In other words, inlet 130 and outlet 132 are configured so as to provide for fluid communication between first tube 120 and second tube 122, respectively, and an interior space of intercostal pump 110.

With reference to FIG. 1B, first tube 120 comprises a tube-inlet end 150 and a pump-inlet end 140. Generally, first tube 120 is configured so that, when intercostal-based fluid management system 100 is in use, tube-inlet end 150 may be disposed in an area of a person's body from which fluid is to be drained. On the other hand, pump-inlet end 140 is coupled to inlet 130 of intercostal pump 110. Accordingly, the length of first tube 120 may vary, as depicted by length extension 160.

Similarly, second tube 122 comprises a pump-outlet end 142 and a tube-outlet end 152. Generally, second tube 122 is configured so that, when intercostal-based fluid management system 100 is in use, tube-outlet end 152 may be disposed in an area of a person's body to which fluid is to be drained. On the other hand, pump-outlet end 142 is coupled to outlet 132 of intercostal pump 110. Accordingly, the length of second tube 122 may vary, as depicted by length extension 162.

Although first tube 120 and second tube 122 are shown as entering into intercostal pump 110 in a substantially straightforward manner, first tube 120 and second tube 122 may be configured to enter intercostal pump 110 at any desired angle. For example, it may be desirable for first tube 120 and second tube 122 to enter and leave, respectively, intercostal pump 110 at ninety-degree angles so as to enable intercostal pump 110 to be situated in the intercostal region in a more advantageous manner. It may be desirable for first tube 120 and second tube 122 to enter and leave at other angles as well.

With reference to FIG. 1C, first tube 120 may comprise one or more fluid-inlet perforations 170. Fluid-inlet perforations 170 may take the form of holes in the surface of first tube 120 allowing for the intake of fluid into first tube 120 through not only tube-inlet end 150, but through fluid-inlet perforations 170 as well. Fluid-inlet perforations 170 may improve the volume or efficiency of fluid intake into first tube 120, and thereby, may improve the volume or efficiency of fluid drained by intercostal-pump based fluid management system 110. Fluid-inlet perforations 170 may be particularly advantageous as allowing for alternative fluid inlet locations in the event that tube-inlet end 150, or other perforations, become blocked due to, for example, clotting.

Second tube 122 may also include fluid-outlet perforations (not depicted).

In order to prevent clogging, the fluid inlets or outlets, the first and second tubes, or any other aspect of inter-costal pump based fluid management system 100 may be coated in anticoagulation factors. For example, the valves of intercostal pump 110 may be coated with anticoagulation factors. The presence of the anticoagulation factors may reduce the amount of clotting that would otherwise occur if they were not present. Examples of anticoagulation factors include tissue plasminogen activator, heparin, urokinase, streptokinase, and warfarin. Other examples of anticoagulation factors may exist as well.

b. Pleuroperitoneal Inter-Costal Pump Based Fluid Management System

Figure 2:
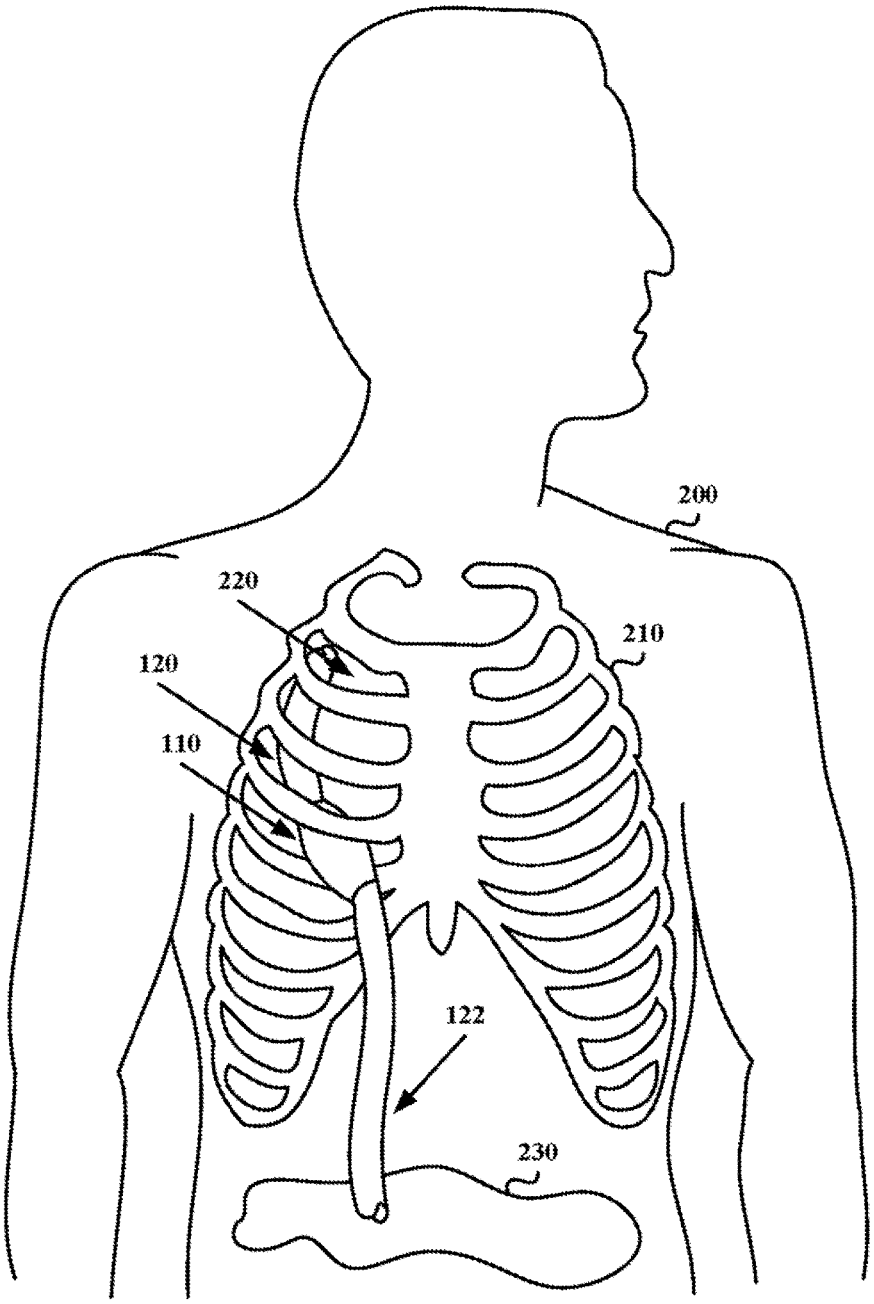
FIG. 2 shows an embodiment of an exemplary intercostal-pump based fluid management system implanted in a patient.

With reference to FIG. 2, intercostal-pump based fluid management system 100 is implanted in a patient 200, providing for drainage of fluid from a first area 220 to a second area 230 within the patient's body. In one embodiment, as in the embodiment depicted in FIG. 2, fluid is drained from a patient's pleural cavity to the patient's peritoneal cavity. In such an embodiment, therefore, first area 220 is the patient's pleural cavity and second area 230 is the patient's peritoneal cavity.

In an embodiment, intercostal pump 110 is configured so that it may be placed, at least partially, in the intercostal region between two ribs. In other words, when implanted, intercostal pump 110 extends throughout the patient's intercostal space, or at least a portion thereof. Accordingly, first tube 120, and correspondingly, pump inlet 130 (not depicted), are disposed on the interior of the patient's rib cage. On the other hand, second tube 122, and correspondingly, pump outlet 132 (not depicted), are disposed on the exterior of the patient's rib cage. In this way, upon breathing and the corresponding compression/decompression of the rib cage, patient 200 will automatically cause intercostal pump 110 to operate (i.e., "pump"). The operation of intercostal pump 110 is discussed further below.

c. Other Inter-Costal Pump Based Fluid Management Systems

A fluid management system that includes intercostal pump 110 may be used for draining fluid from and to various areas of a patient's body. That is, a fluid management system that includes the intercostal pump described herein is not limited to uses involving draining fluid from a patient's pleural cavity to the patient's peritoneal cavity.

One example of an alternative use of a fluid management system that incorporates the intercostal pump described herein is draining fluid from a patient's cerebrospinal region. According to this exemplary alternative use, tube 120 may be configured to extend from intercostal pump 110 to the patient's cerebrospinal region such that tube-inlet end 150 may be disposed in the patient's cerebrospinal region. In this way, excess cerebrospinal fluid may be drained.

Another example of an alternative use of a fluid management system that incorporates the inter-costal pump described herein is draining fluid from a patient's pericardial region.

Other alternative uses are certainly possible as well. In general, a fluid management system that incorporates the intercostal pump described herein may be used to drain fluid to and from any combination of regions in a patient's body with which fluid communication can be sufficiently established with intercostal pump 110.

2. THE INTERCOSTAL PUMP a. Intercostal Pump Design

Figure 3A:
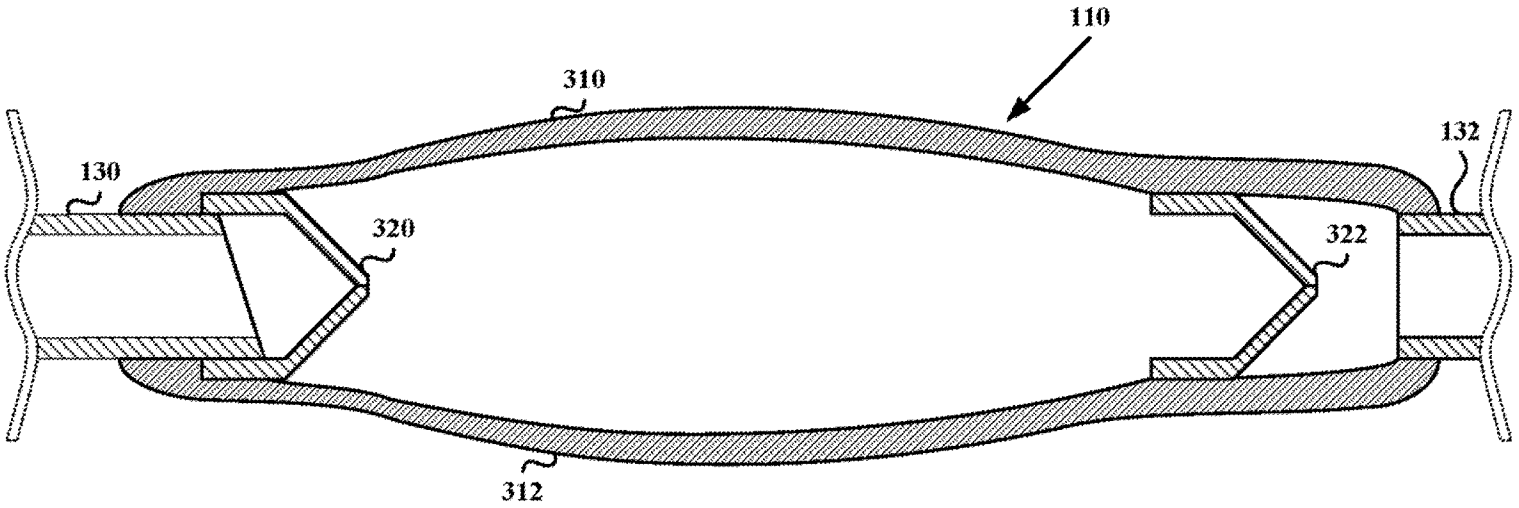
FIGS. 3A, 3B, and 3C show a cross-sectional schematic view of an exemplary intercostal-pump body.

FIG. 3A shows an exemplary cross-sectional schematic view of intercostal pump 110. As noted above, intercostal pump 110 is, generally, a resiliently flexible bulb. As such, the pump body, as well as any of the other various pump components, may be made of polyurethane, silicone, polyvinyl chloride, or latex rubber. Other materials are certainly possible as well.

Intercostal pump 110 comprises a pump wall that encloses an interior space 330. For purposes of explanation, the pump wall is depicted as including upper wall 310 and lower wall 312. The distinction between an upper and lower wall is made for the purposes of clarity in explaining the compression/decompression of intercostal pump 110 below, and should not be interpreted as limiting intercostal pump 110 to comprise two distinct pump walls.

Generally, pump wall 310 (312) may be of any thickness suitable to achieve desired flexibility of intercostal pump 110. The particular thickness of pump wall 310 (312) in a given embodiment may depend on, for example, the material of pump wall 310 (312) and the intended use (e.g., drainage function) of intercostal pump 110. In an embodiment, pump wall 310 (312) may be made of silicon and have a thickness of 1/32 of an inch. In an embodiment, intercostal pump 110 may comprise silicone tubing having an inner diameter of 1/4 of an inch and an outer diameter of 5/16 of an inch. Other dimensions may be desirable as well.

Intercostal pump 110 further comprises inlet valve 320 and outlet valve 322. Inlet valve 320 may be situated in the interior space 330 of the pump body in general proximity to inlet 130. Inlet valve 320 may be any suitable one-way valve, and may, for example, be made of silicone. Inlet valve 320 is configured so as to preclude fluid movement from the interior space 330 of intercostal pump 110 to inlet tube 130. At the same time, inlet valve 320 is configured to allow fluid movement from inlet tube 130 to the interior space 330 of intercostal pump 110. In other words, inlet valve 320 is in fluid communication with inlet 130 so as to provide for one-way fluid movement from inlet tube 130 to interior space 330 of intercostal pump 110.

Correspondingly, outlet valve 322 may be situated in the interior space 330 of the pump body in general proximity to outlet 132. Outlet valve 322 may be any suitable one-way valve, and may, for example, be made of silicone. Outlet valve 322 is configured so as to allow fluid movement from the interior space 330 of intercostal pump 110 to outlet tube 132. At the same time, outlet valve 322 is configured to prevent fluid movement from outlet tube 132 to the interior space 330 of intercostal pump 110. In other words, outlet valve 322 is in fluid communication with outlet 132 so as to provide for one-way fluid movement from interior space 330 of intercostal pump 110 to outlet tube 132.

It may be desirable to reinforce the outer perimeter of inlet valve 320 and outlet valve 322 so that the compression/decompression of intercostal pump 110 does not cause significant compression of, or undesirable wear to, inlet valve 320 and outlet valve 322. Such reinforcement may be accomplished, for example, by using a relatively stiff, or non-flexible material, for the outer perimeter of inlet valve 320 and outlet valve 322. Other examples may exist as well Note that, although inlet valve 320 and outlet valve 322 are depicted as situated within the interior space 330 of intercostal pump 110, alternative placement of the valves may be desirable as well. For example, one of, or both of, inlet valve 320 and outlet valve 322 might be situated exterior to the pump body, perhaps within inlet tube 130 and outlet tube 132, respectively. The particular placement of the valves is not critical, so long as they sufficiently provide for one-way fluid flow into and out of intercostal pump 110.

b. Pump Operation

Figure 3B:
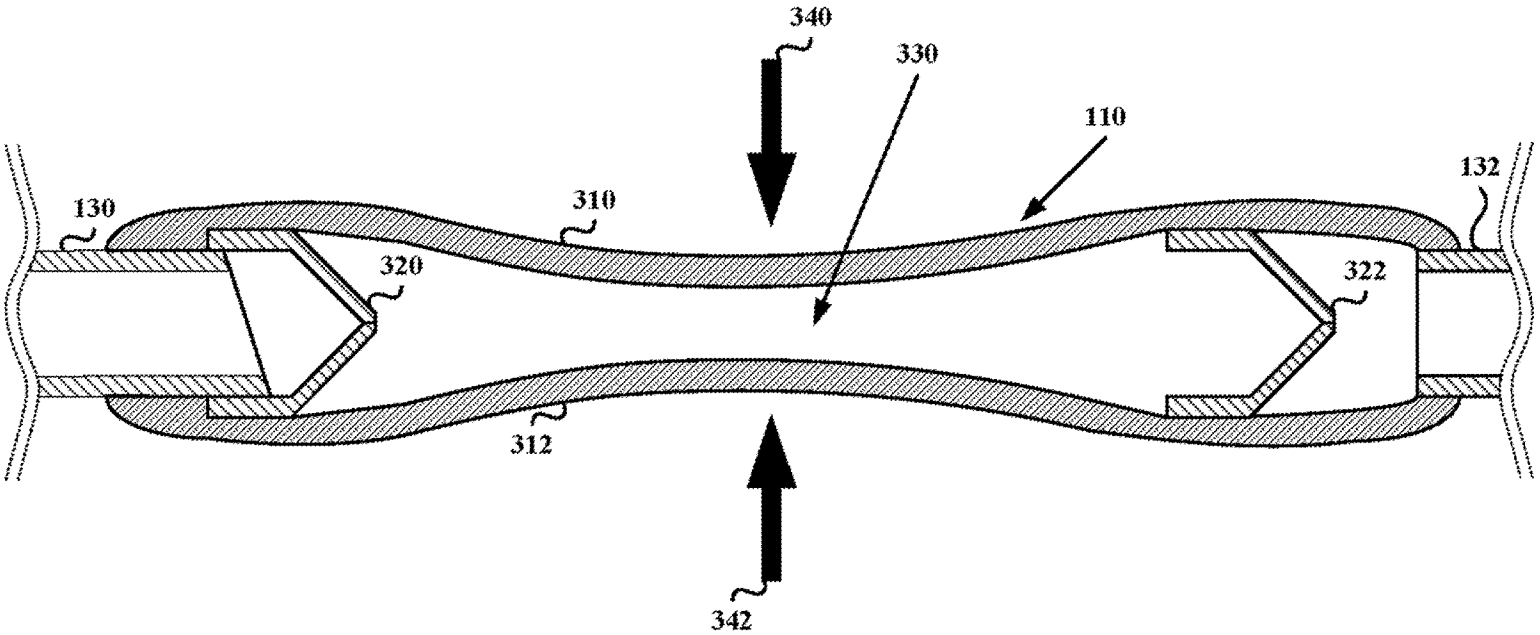

FIG. 3B shows an exemplary cross-sectional schematic view of intercostal pump 110 in a compressed state. In an exemplary embodiment, as shown, a first force 340 acts on upper wall 310 causing upper wall 310 to collapse in towards interior space 330. Correspondingly, a second force 342 acts on lower wall 312 causing lower wall 312 to collapse in towards interior space 330. As described above, intercostal pump 110 is resiliently flexible and therefore, after being placed in a compressed state as shown in FIG. 3B, intercostal pump 110 will return to an uncompressed state as shown in FIG. 3A when at least one of the first force 340 and the second force 342 are removed. In this way, intercostal pump 110 operates as a pump that, generally, draws fluid from its inlet 130 to its outlet 132.

In use, intercostal pump 110 may be compressed as a result of a patient breathing. More particularly, intercostal pump 110 may be compressed as a result of the natural movement of a patient's ribs during the breathing cycle.

Figure 3C:
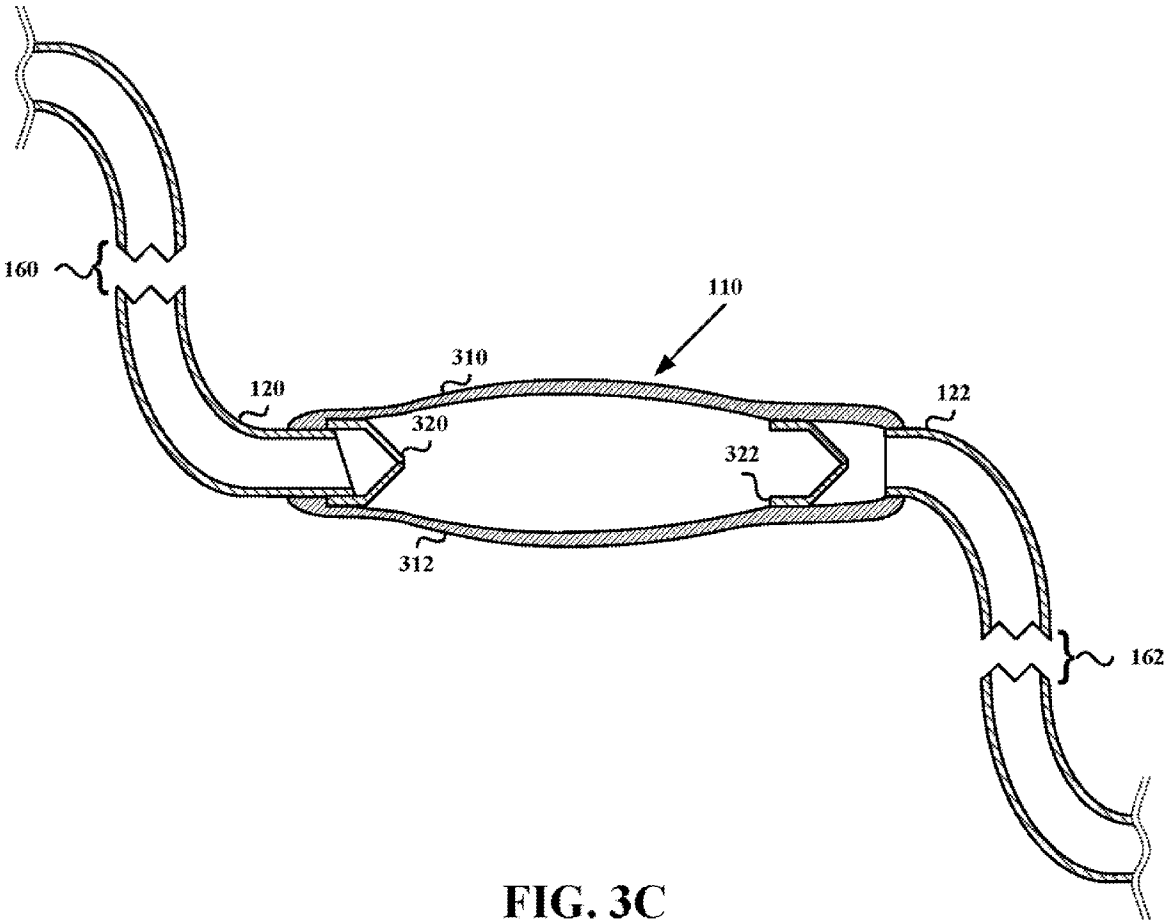

FIG. 3C shows an exemplary cross-sectional schematic view of intercostal pump 110 and tubes 120 and 122 having length extensions 160 and 162, respectively. FIG. 3C general shows tubes 120 and 122 as generally flexible tubing that may be easily manipulated and/or shaped to take any form or direction. However, in some embodiments it may be desirable for tubes 120 and 122 to be rigidly defined, to some extent, so that a desired shape or direction of the tubes may be maintained. For example, one of the tubes may be rigidly configured, shaped, or cast so that it has a 90 degree bend upon leaving intercostal pump 110. Each of tubes 120 and 122 may be configured to a similar 90 degree bend. Alternatively, the tubes may not have similar bends. As yet another alternative, the tubes may each have a bend of some other degree.

Figure 4A:
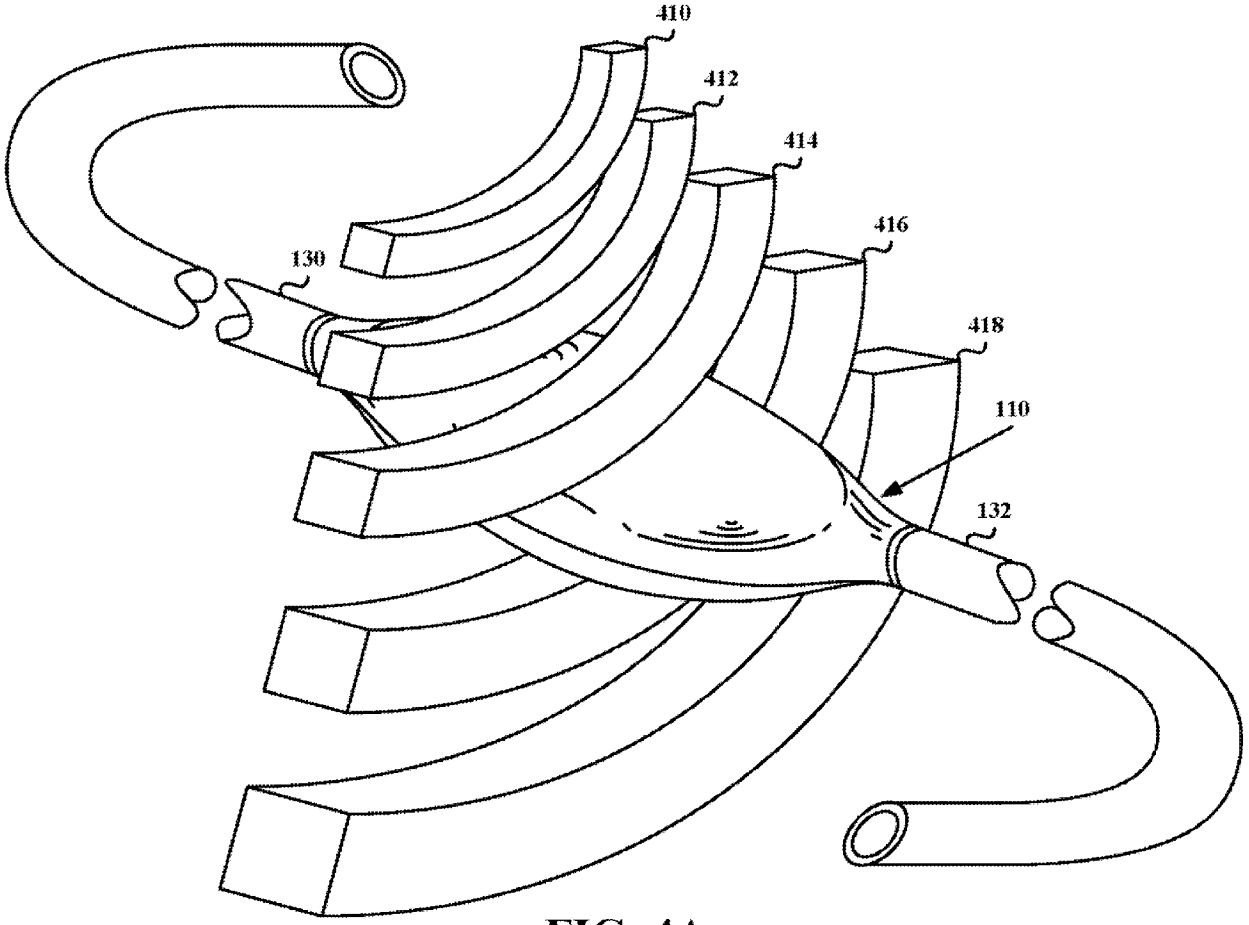
FIGS. 4A and 4B show a focused view of an exemplary intercostal-pump based fluid management system placed between a patient's ribs, and the intercostal pump activated thereby.

As shown in FIG. 4A, in use, intercostal pump 110 is placed between a first rib 416 and a second rib 418. When the rib cage expands (upon inhaling), individual ribs 410, 412, 414, 416, and 418 separate and relatively little force is exerted on intercostal pump 110. Therefore, intercostal pump 110 is in an uncompressed state.

Figure 4B:
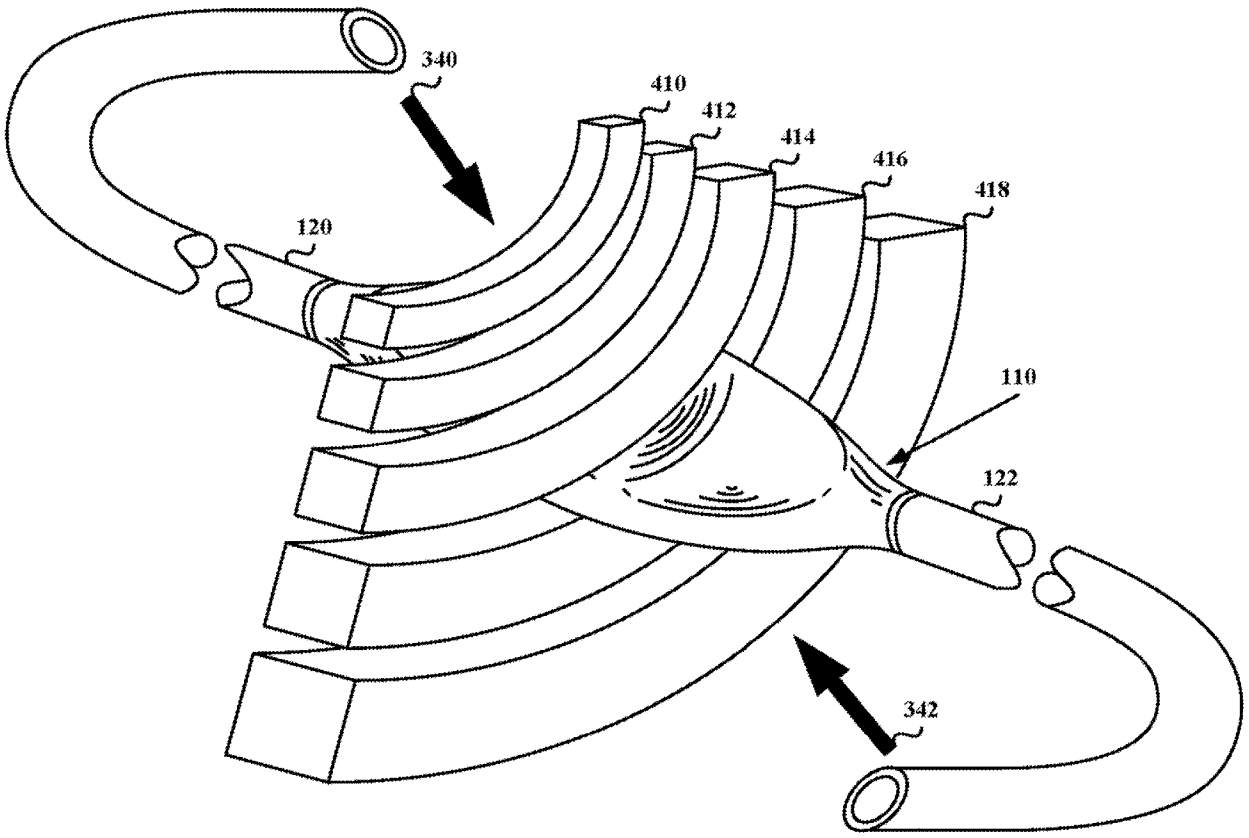

However, as shown in FIG. 4B, when the rib cage contracts (upon exhaling), individual ribs 410, 412, 414, 416, and 418 move towards one another. As a result, a first force 340 and a second force 342 are exerted on intercostal pump 110 by first rib 416 and second rib 418 respectively. Therefore, intercostal pump 110 is in a compressed state.

A normal adult takes about twelve breaths per minute. Therefore, in use, intercostal pump 110 may be compressed approximately twelve times per minute. Of course, this is only an approximation and may vary greatly. A particular compression rate is not critical to the functioning of intercostal pump 110, though the rate at which fluid is pumped will obviously vary with the compression rate and amplitude of compression (i.e., degree of rib motion).

A normal adult exhibits approximately two millimeters of relative motion between ribs throughout the breathing cycle. Accordingly, the walls of intercostal pump 110 may be compressed approximately two millimeters during each breath. Of course, this is only an approximation and may vary greatly.

A relevant consideration is that ribs are lined by soft tissue. The soft tissue may be compressible itself and therefore, if any soft tissue is left in place between intercostal pump 110 and either of first rib 416 and second rib 418, the full extent of possible compression of intercostal pump 110 may not be achieved. It may therefore be desirable to remove soft tissue at the point of contact of intercostal pump 110 with either of first rib 416 and second rib 418.

Another relevant consideration is that ribs generally exhibit portions that are relatively cartilaginous, which portions may be relatively compressible themselves. As a result, it may be desirable to place intercostal pump 110 so as to be in contact with portions of first rib 416 and second rib 418 exhibiting a relatively low amount of cartilage (i.e., a portion of the rib having a relatively high amount of bone, as opposed to cartilage, exposed).

Yet another relevant consideration is that it may be desirable to situate intercostal pump 110 in such way that the amount of surface area of intercostal pump 110 that is in contact with each of first rib 416 and second rib 418 is maximized. In this way, intercostal pump 110 may experience a greater amount of compression. Therefore, it may be desirable to situate intercostal pump 110 in a manner substantially parallel to first rib 416 and second rib 418 as opposed to the substantially perpendicular manner as generally indicated in FIGS. 4A and 4B.

3. OTHER INTER-COSTAL PUMP BASED FLUID MANAGEMENT SYSTEM ARRANGEMENTS

As a patient breaths, the patients' pleural space expands and contracts. Accordingly, the pressure within the pleural space decreases and increases, relatively. Such changes in the pressure within the pleural space may be used to activate a pump that is located within the pleural space. Thus, a pump within the pleural space may be activated by such changes in the pressure within the pleural space. These pressure changes may activate a pump independently of, or in combination with, any activation caused by compression due to displacement of the patients' ribs as discussed above.

Similarly, as a patient breaths, the patients' abdomen expands and contracts. Accordingly, the pressure within the abdomen decreases and increases, relatively. Such changes in the pressure within the abdomen may be used to activate a pump that is located within the abdomen. Thus, a pump within the abdomen may be activated by such changes in pressure within the abdomen.

Figure 6:
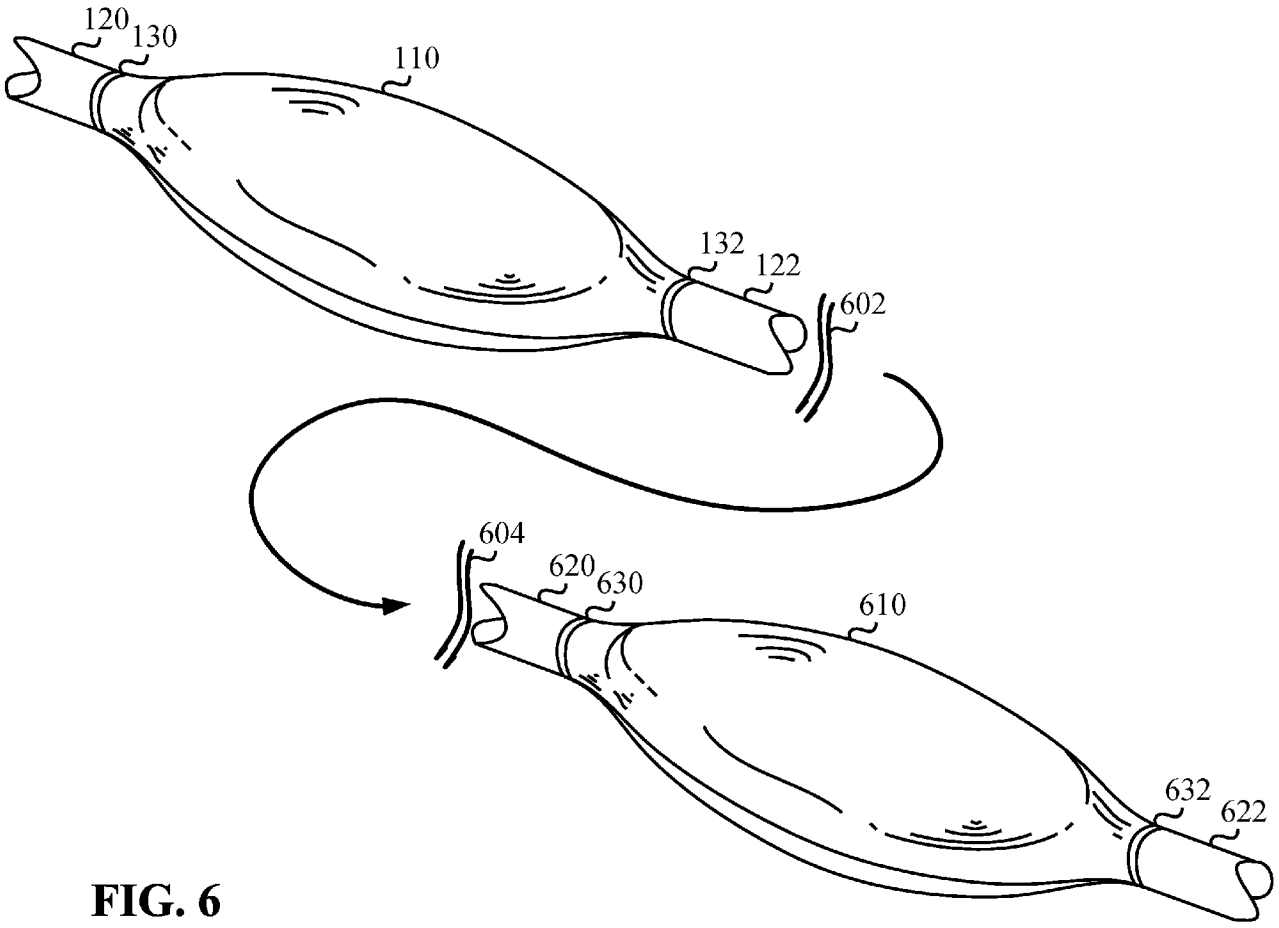
FIG. 6 shows a perspective view of an additional exemplary intercostal-pump based fluid management system.

As shown in FIG. 6, the inter-costal pump based fluid management system may include two pumps 110 and 610. According to such a system, pump 110 may be placed within a patient's pleural space, perhaps within an intercostal region as discussed above. Pumps 110 and 610 may be communicatively couple at points 602 and 604, respectively. Pumps 110 and 610 may be communicatively coupled by an extendible tube, or a tube a given desired length. Pump 610 may then be placed within a patient's abdomen. As a result, pump 110 may be activated by one or more of compression due to the patient's rib compression or pressure change within the patient's pleural space, and pump 610 may be activated by pressure change within the patient's abdomen.

Such a system including two pumps (such as that shown in FIG. 6) may be capable of achieving greater overall pump force than may be a system including a single pump (such as shown in FIG. 1C.

4. EXEMPLARY METHODS a. First Exemplary Method

A method of draining a fluid from a first area of a person's body to a second area of a person's body may be carried out with respect to intercostal-pump based fluid management system 100.

Figure 5A:
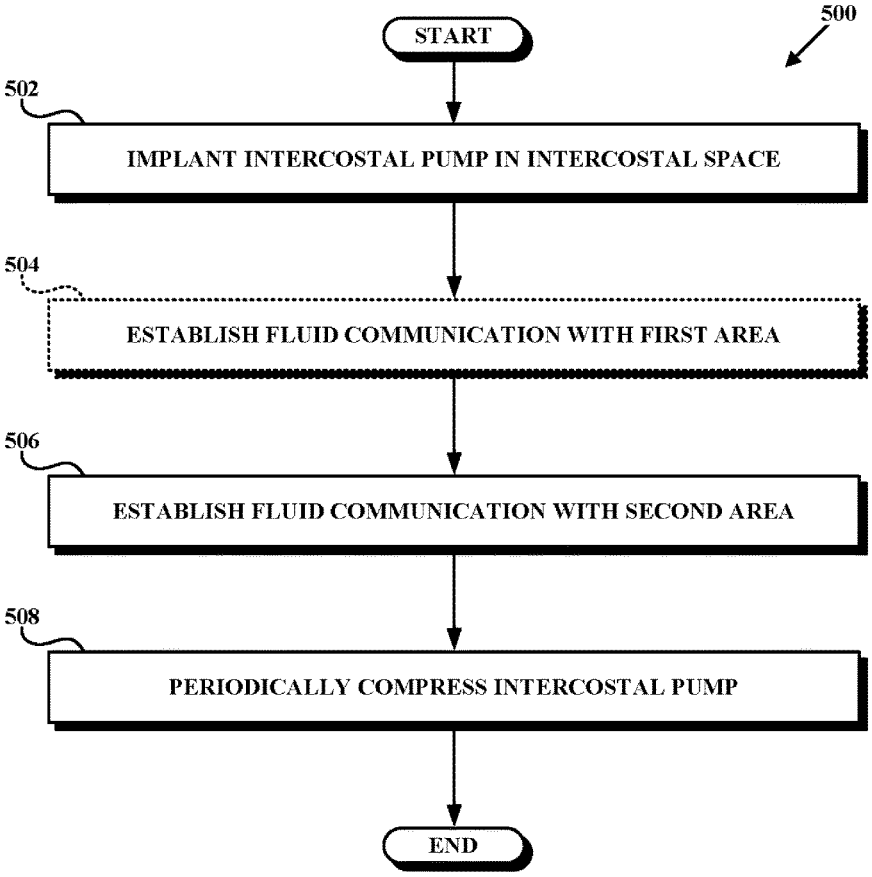
FIGS. 5A and 5B show exemplary methods for draining bodily fluid.

With reference to FIG. 5A and method 500, at step 502, intercostal pump 110 is implanted in an intercostal space of a patient such that the intercostal pump may be compressed between first rib 416 and second rib 418. Intercostal pump 100 may be implanted using known surgical techniques.

At step 504, fluid communication is established between a first area of a patient and the inlet 130 of intercostal pump 110. For example, first tube 120 may be extended from a patient's pleural cavity to inlet 130.

At step 506, fluid communication is established between a second area of a patient and the outlet 132 of intercostal pump 110. For example, second tube 122 may be extended from outlet 132 to a patient's peritoneal cavity.

At step 508, intercostal pump 110 is periodically compressed. For example, intercostal pump 110 is compressed between first rib 416 and second rib 418 during a patient's breathing cycle.

b. Second Exemplary Method

Figure 5B:
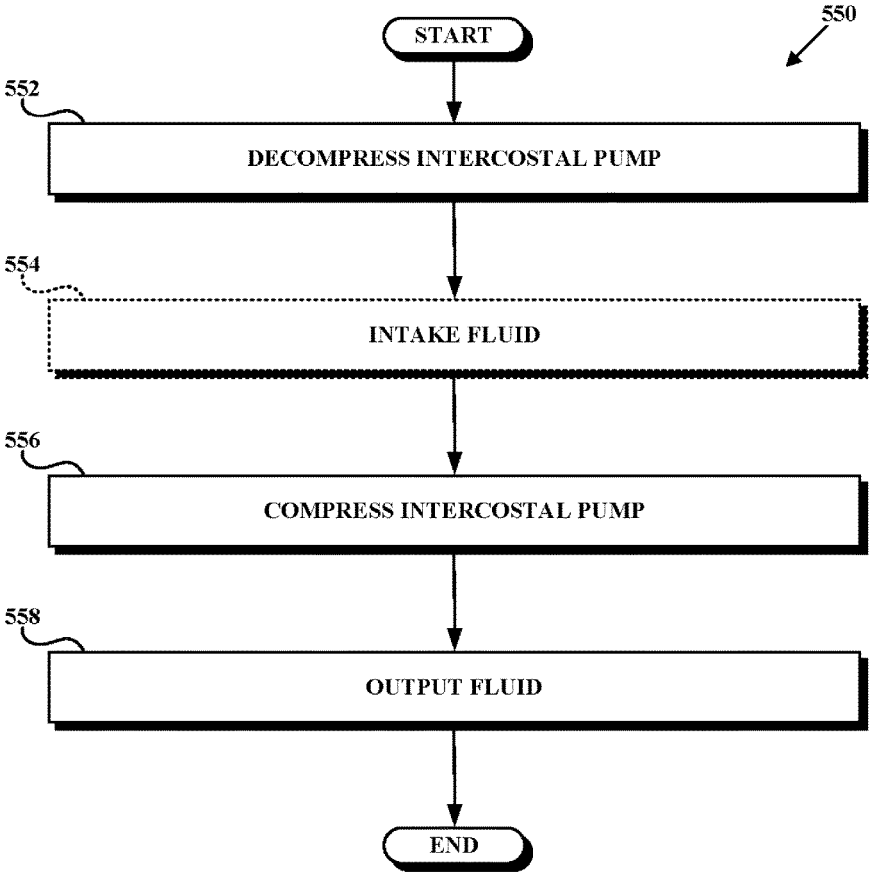

With reference to FIG. 5B and method 550, at step 552, intercostal pump 110 is decompressed. For example, intercostal pump 110 is initially compressed between first rib 416 and second rib 418 while a patient's ribs are in a contracted stated (i.e., the patient has previously exhaled). As the patient inhales, the rib cage is expanded and first rib 416 and second rib 418 move away from one another. As a result, intercostal pump 110 is decompressed.

At step 554, intercostal pump 110 intakes fluid. That is, as a result of decompressing intercostal pump 110 at step 552, a pumping force draws fluid into interior space 330 of intercostal pump 110.

At step 556, intercostal pump 110 is compressed. For example, intercostal pump 110 is compressed between first rib 416 and second rib 418 as a result of the patient's rib cage being contracted (i.e., the patient exhales). As the patient exhales, the rib cage is contracted and first rib 416 and second rib 418 move towards one another. As a result, intercostal pump 110 is compressed.

At step 558, intercostal pump 110 outputs fluid. That is, as a result of compressing intercostal pump 110 at step 556, a pumping force forces fluid out of interior space 330 of intercostal pump 110.

5. CONCLUSION

Exemplary embodiments of an intercostal-pump based fluid management system are described above. Those skilled in the art will understand, however, that changes and modifications may be made to the embodiments described without departing from the true scope and spirit of the present invention, which is defined by the claims.

The invention claimed is:

1. A method comprising:

implanting in an intercostal space of a *body of a* person an intercostal pump [such that the intercostal pump may be compressed between a first rib of the person and a second rib of the person], *wherein* the intercostal pump [comprising] (*i*) *comprises a pump body,* an inlet, and an outlet *and* (*ii*) *is configured such that, as the person breathes, the pump body is compressed and decompressed between a first rib and a second rib of the person's body and thereby induces fluid flow* (*a*) *from a pleural cavity of the person's body via a first tube connected to the inlet* (*b*) *to a peritoneal cavity of the person's body via a second tube connected to the outlet*; and establishing fluid [communication] *flow* (a) between [a] *the* pleural cavity of the person's body and the inlet [with a] *via the* first tube and (b) between the outlet and [a] *the* peritoneal cavity of the person's body [with a] *via the* second tube.

2. The method of claim 1, further comprising:

configuring the intercostal pump for placement in the intercostal space so as to be activated by being compressed by (a) the first rib at a first point of contact between the first rib and the intercostal pump and (b) the second rib at a second point of contact between the second rib and the intercostal pump.

3. The method of claim 1, wherein the intercostal pump is configured for placement in the intercostal space so as to be activated by being compressed by (a) the first rib at a first point of contact between the first rib and the intercostal pump and (b) the second rib at a second point of contact between the second rib and the intercostal pump.

4. The method of claim 1, wherein the intercostal pump comprises a first one-way valve in fluid-flow communication with the inlet and a second one-way valve in fluid-flow communication with the outlet, the first one-way valve configured to preclude material movement from a bulb to the first tube, and the second one-way valve configured to preclude material movement from the second tube to the bulb.

5. The method of claim 1, further comprising:

extending the first tube from the pleural cavity of the [person] *person's body* to the inlet.

6. The method of claim 1, further comprising:

extending the second tube from the outlet to the peritoneal cavity of the person.

7. The method of claim 1, further comprising:

adjusting the length of one or each of the first tube or the second tube.

8. The method of claim 1, further comprising:

coating one or more of the intercostal pump, the first tube, or the second tube in anticoagulation factors.

9. The method of claim 1, wherein implanting in the intercostal space of the [person] *person's body* the intercostal pump such that the intercostal pump may be compressed between the first rib and the second rib comprises implanting in the intercostal space of the [person] *person's body* the intercostal pump such that an amount of surface area of intercostal pump that is in contact with each of the first rib and the second rib is maximized.

10. The method of claim 1, wherein the intercostal pump comprises one or more of polyurethane, silicone, polyvinyl chloride, or latex rubber.

11. The method of claim 1, wherein the first tube comprises at least one fluid-inlet perforation along its surface.

12. The method of claim 1, wherein implanting in the intercostal space of the [person] *person's body* the intercostal pump comprises implanting the intercostal pump such that the inlet and the first tube are each at least partially disposed on the interior of a rib cage of the person's body.

13. The method of claim 1, wherein implanting in the intercostal space of the [person] *person's body* the intercostal pump comprises implanting the intercostal pump such that the outlet and the second tube are at least partially disposed on the exterior of a rib cage of the person's body.

14. The method of claim 1, wherein the intercostal pump comprises at least one resiliently flexible pump wall.

15. The method of claim 1, wherein one or each of an outer perimeter of the inlet and [the] *an* outer perimeter of the outlet comprises a non-flexible material.

16. The method of claim 1, further comprising:

removing soft tissue from the intercostal space.

17. The method of claim 1, wherein implanting in the intercostal space of the [person] *person's body* the intercostal pump comprises implanting the intercostal pump such that it is substantially parallel to the first rib and the second rib.

18. The method of claim 1, wherein implanting in the intercostal space of the [person] *person's body* the intercostal pump comprises implanting the intercostal pump such that it is substantially perpendicular to the first rib and the second rib.

19. A method comprising:

implanting in an intercostal space of a *body of a* person an intercostal pump [such that the intercostal pump may be compressed between a first rib of the person and a second rib of the person], *wherein* the intercostal pump [comprising] (*i*) *comprises a pump body,* an inlet, and an outlet *and* (*ii*) *is configured such that, as the person breathes, the pump body is compressed and decompressed between a first rib and a second rib of the person's body and thereby induces fluid flow* (*a*) *from a first cavity of the person's body via a first tube connected to the inlet* (*b*) *to a second cavity of the person's body via a second tube connected to the outlet, and* wherein the intercostal pump comprises silicone[, and wherein the first tube comprises at least one fluid-inlet perforation along its surface]; and establishing fluid [communication] *flow* (a) between [a pleural] *the first* cavity of the person's body and the inlet [with a] *via the* first tube, *wherein the first tube comprises at least one fluid-inlet perforation along its surface* and (b) between the outlet and [a peritoneal] *the second* cavity of the person's body [with a] *via the* second tube.

20. A method comprising:

implanting in an intercostal space of a *body of a* person an intercostal pump [such that the intercostal pump may be compressed between a first rib of the person and a second rib of the person], *wherein* the intercostal pump [comprising] (*i*) *comprises a pump body,* an inlet, and an outlet *and* (*ii*) *is configured such that, as the person breathes, the pump body is compressed and decompressed between a first rib and a second rib of the person's body and thereby induces fluid flow* (*a*) *from a first cavity of the person's body via a first tube connected to the inlet* (*b*) *to a second cavity of the person's body via a second tube connected to the outlet*; and establishing fluid [communication] *flow* between (a) [a pleural] *the first* cavity of the person's body and the inlet [with a] *via the* first tube and (b) between the outlet and [a peritoneal] *the second* cavity of the person's body [with a] *via the* second tube, wherein implanting in the intercostal space of the [person] *person's body* the intercostal pump comprises implanting the intercostal pump such that (a) the inlet and the first tube are each at least partially disposed on the interior of a rib cage of the person's body and (b) the outlet and the second tube are at least partially disposed on the exterior of a rib cage of the person's body.

*21. The method of claim 19, wherein the first cavity comprises a pleural cavity of the person's body and the second cavity comprises a peritoneal cavity of the person's body.*

*22. The method of claim 20, wherein the first cavity comprises a pleural cavity of the person's body and the second cavity comprises a peritoneal cavity of the person's body.*

*23. An intercostal pump comprising:*

*a compressible pump body that is configured for placement in an intercostal region between two ribs of a body of a person;*

*an inlet adapted for attachment to a first tube that is to extend between the intercostal pump and a pleural cavity of the person's body; and*

*an outlet adapted for attachment to a second tube that is to extend between the intercostal pump and a peritoneal cavity of the person's body,*

*wherein the intercostal pump is configured such that, as the person breathes, the compressible pump body is compressed and decompressed between the two ribs of the person's body and thereby induces fluid flow (a) from the pleural cavity of the person's body via the first tube (b) to the peritoneal cavity of the person's body via the second tube.*

*24. The intercostal pump of claim 23, wherein the compressible pump body comprises at least one resiliently flexible pump wall that encloses an interior space.*

*25. The intercostal pump of claim 23, further comprising:*

*a first one-way valve that is in fluid-flow communication with the inlet and is configured to preclude material movement from the compressible pump body to the first tube; and*

*a second one-way valve that is in fluid-flow communication with the outlet and is configured to preclude material movement from the second tube to the compressible pump body.*

*26. The intercostal pump of claim 23, wherein at least a portion of the intercostal pump is coated in anticoagulation factors.*

*27. The intercostal pump of claim 23, wherein the intercostal pump is made from one or more of polyurethane, silicone, polyvinyl chloride, or latex rubber.*

*28. A fluid management system comprising:*

*an intercostal pump comprising a compressible pump body, an inlet, and an outlet, wherein the intercostal pump is configured to be implanted in an intercostal space between two ribs of a body of a person;*

*a first tube configured to extend between the inlet of the intercostal pump and a pleural cavity of the person's body; and*

*a second tube configured to extend between the outlet of the intercostal pump and a peritoneal cavity of the person's body,*

*wherein the intercostal pump is configured such that, as the person breathes, the compressible pump body is compressed and decompressed between the two ribs of the person's body and thereby induces fluid flow (a) from the pleural cavity of the person's body via the first tube (b) to the peritoneal cavity of the person's body via the second tube.*

*29. The fluid management system of claim 28, wherein the first tube comprises at least one fluid-inlet perforation along its surface.*

*30. The fluid management system of claim 29, wherein the intercostal pump is configured to be implanted in the intercostal space between the two ribs of the person's body such that (a) the inlet and the first tube are each at least partially disposed on the interior of a rib cage of the person's body and (b) the outlet and the second tube are at least partially disposed on the exterior of a rib cage of the person's body.*

* * * * *